(12) United States Patent
Demianovich

(10) Patent No.: US 10,367,403 B2
(45) Date of Patent: Jul. 30, 2019

(54) SYSTEMS AND METHODS FOR INDEPENDENT MOTION OF PARALLEL ACTUATORS

(71) Applicant: General Electric Company, Schenectady, NY (US)

(72) Inventor: Nicholas Demianovich, Waukesha, WI (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 1087 days.

(21) Appl. No.: 14/465,069

(22) Filed: Aug. 21, 2014

(65) Prior Publication Data
US 2016/0056700 A1 Feb. 25, 2016

(51) Int. Cl.
*H02K 41/02* (2006.01)
*G21K 1/02* (2006.01)
*A61B 6/06* (2006.01)
*H02K 41/00* (2006.01)
*G21K 1/04* (2006.01)

(52) U.S. Cl.
CPC ............ *H02K 41/02* (2013.01); *A61B 6/06* (2013.01); *G21K 1/02* (2013.01); *G21K 1/04* (2013.01); *G21K 1/046* (2013.01); *H02K 41/00* (2013.01)

(58) Field of Classification Search
CPC ... A61B 6/06; G21K 1/02; G21K 1/04; G21K 1/043; G21K 1/046; H02K 41/00; H02K 41/02; H02K 41/025; H02K 41/03; H02K 41/031; H02K 41/033; H02K 41/035; H02K 41/0352; H02K 41/0354; H02K 41/0356; H02K 41/0358; H02K 41/06; H02K 41/065

USPC ....... 378/147, 148, 149, 150, 151, 152, 153, 378/154, 155, 156, 157, 158, 159, 160, 378/161; 310/12.01, 12.02, 12.04, 12.05, 310/12.06, 12.07, 12.08, 12.09, 12.11, 310/12.12, 12.13, 12.14, 12.15
See application file for complete search history.

(56) References Cited

U.S. PATENT DOCUMENTS

| 3,261,480 | A | | 7/1966 | Haaker et al. |
| 4,713,887 | A | | 12/1987 | Kitamura |
| 4,766,603 | A | * | 8/1988 | Okabe .................... A61B 6/022 378/150 |
| 5,396,534 | A | * | 3/1995 | Thomas ................... G21K 1/04 378/147 |
| 6,150,740 | A | | 11/2000 | Slocum |
| 2005/0141671 | A1 | * | 6/2005 | Pastyr ..................... G21K 1/04 378/148 |
| 2007/0086575 | A1 | * | 4/2007 | Xu .......................... A61B 6/06 378/147 |

(Continued)

Primary Examiner — Bernard Rojas
Assistant Examiner — Alexander A Singh
(74) Attorney, Agent, or Firm — Fletcher Yoder, P.C.

(57) ABSTRACT

Techniques for independent motion actuator are described herein. The techniques may include a first linear actuator, a first driven carriage to be driven by movement of the first linear actuator, and a first free carriage in line with the first linear actuator but being disengaged from the first linear actuator. The techniques may also include a second linear actuator substantially parallel to the first linear actuator. A second driven carriage is to be driven by movement of the second linear actuator, and a second free carriage in line with the second linear actuator but being disengaged from the second linear actuator and to be coupled to the first driven carriage.

18 Claims, 5 Drawing Sheets

(56) References Cited

U.S. PATENT DOCUMENTS

2008/0292058 A1* 11/2008 Nagata .................. G21K 1/046
378/152

* cited by examiner

200

SYSTEMS AND METHODS FOR INDEPENDENT MOTION OF PARALLEL ACTUATORS

BACKGROUND OF THE INVENTION

The subject matter disclosed herein relates generally to techniques for independent motion in parallel actuators. In various systems, rotational motion may translate into linear motion via a linear actuator. For example, in a collimator of a medical imaging system, two parallel actuators may be coupled to two plates that are perpendicular to the actuators. The plates may be moved to open and close an aperture of the collimator. However, independent control of each plate is difficult to obtain without increased bulk resulting from independent control mechanisms.

In general, for linear motion systems, independent control, alignment, accuracy, and package size are all design challenges. Independent control of parallel actuators may include multiple actuators and multiple bearing supports, which must be independently aligned.

BRIEF DESCRIPTION OF THE INVENTION

An embodiment relates to an apparatus for independent actuator motion. The apparatus includes a first linear actuator and a second linear actuator substantially parallel to the first linear actuator. The apparatus also includes a first driven carriage to be driven by movement of the first linear actuator, and a first free carriage in line with the first linear actuator but being disengaged from the first linear actuator motion. The apparatus includes a second driven carriage to be driven by movement of the second linear actuator. The apparatus also includes a second free carriage in line with the second linear actuator but being disengaged from the second linear actuator movement. The second free carriage is to be coupled to the first driven carriage.

Another embodiment relates to a system for independent actuator motion. The system includes a first actuator assembly and a second actuator assembly substantially parallel to the first actuator assembly. The first actuator assembly includes a first linear actuator, a first driven carriage to be driven by the first linear actuator, and a first free carriage disengaged from the first linear actuator motion. The second actuator assembly includes a second linear actuator, a second driven carriage to be driven by the second linear actuator, and a second free carriage disengaged from motion associated with the second linear actuator. The second free carriage is coupled to the first driven carriage of the first actuator assembly.

Still another embodiment relates to a method of manufacturing an independent actuator motion apparatus. The method includes forming a first actuator assembly and forming a second actuator assembly substantially parallel to the first actuator assembly. The first actuator assembly includes a first linear actuator, a first driven carriage to be driven by the first linear actuator, and a first free carriage disengaged from the first linear actuator motion. The second actuator assembly includes a second linear actuator, a second driven carriage to be driven by the second linear actuator, and a second free carriage disengaged from motion associated with the second linear actuator. The second free carriage is coupled to the first driven carriage of the first actuator assembly.

BRIEF DESCRIPTION OF THE DRAWINGS

The present techniques will become more fully understood from the following detailed description, taken in conjunction with the accompanying drawings, wherein like reference numerals refer to like parts, in which.

DETAILED DESCRIPTION OF THE INVENTION

In the following detailed description, reference is made to the accompanying drawings that form a part hereof, and in which is shown by way of illustration of specific embodiments that may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken as limiting the scope of the embodiments described herein.

As discussed above, a collimator in a medical imaging system may use parallel actuators having plates attached perpendicular to the actuators to open and close an aperture of the collimator. The opening and closing of the aperture of the collimator may serve to adjust slice thickness of for a given imaging system protocol. In some systems, motors are attached to opposite sides of respective parallel actuators to achieve independent motion of the plates. In the embodiments described herein, independent motion of the plates is achieved by disposing the motors on the same side of parallel actuators, and by placement of a free carriage and a driven carriage on each actuator. In embodiments, placement of a free carriage and a driven carriage on one parallel actuator may be opposite to an arranged placement of a free carriage and a driven carriage on a second parallel actuator. It should be noted that although the various embodiments are described in connection with an imaging system, the various embodiments may be implemented in connection with other wherein independent motion of components, such as plates perpendicular to the parallel actuators, is desired.

Figure 1:
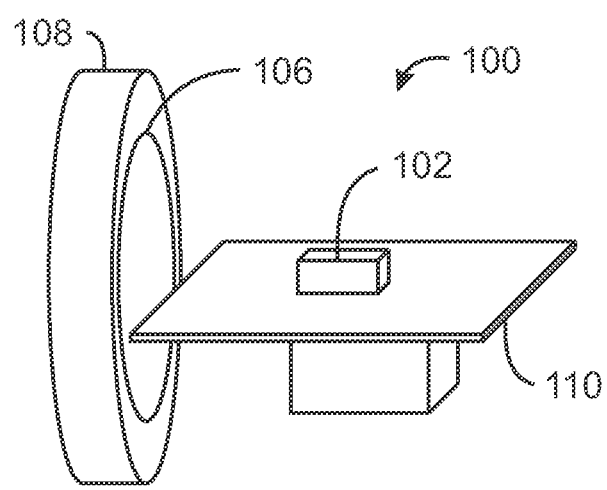
FIG. 1 illustrates perspective view of a diagram of a medical imaging system.

FIG. 1 illustrates perspective view of a diagram of a medical imaging system. In the system 100, a subject 102 can be a human patient in one embodiment. It should be noted that the subject 102 does not have to be human. In embodiments, the subject is some other living creature or inanimate object. As illustrated in FIG. 1, the subject 102 can be placed on a pallet 104 that can move a subject horizontally for locating the subject 102 in the most advantageous imaging position within a bore 106 of a gantry 108. The bed mechanism 110 can raise and lower the pallet 104 vertically for locating the subject in the most advantageous imaging position. The gantry 108 is shown as circular in one embodiment. In other embodiments the gantry 108 may be of any shape such as square, oval, "C" shape, a hexagonal shape, and the like.

Although not illustrated in FIG. 1, the gantry 108 may include a radiation emitter and a collimator. As discussed in more detail below, the collimator may include a number of parallel actuators configured with plates attached perpendicular to the actuators to adjust an aperture of the collimator defined by the distance between the perpendicularly attached plates.

Figure 2:
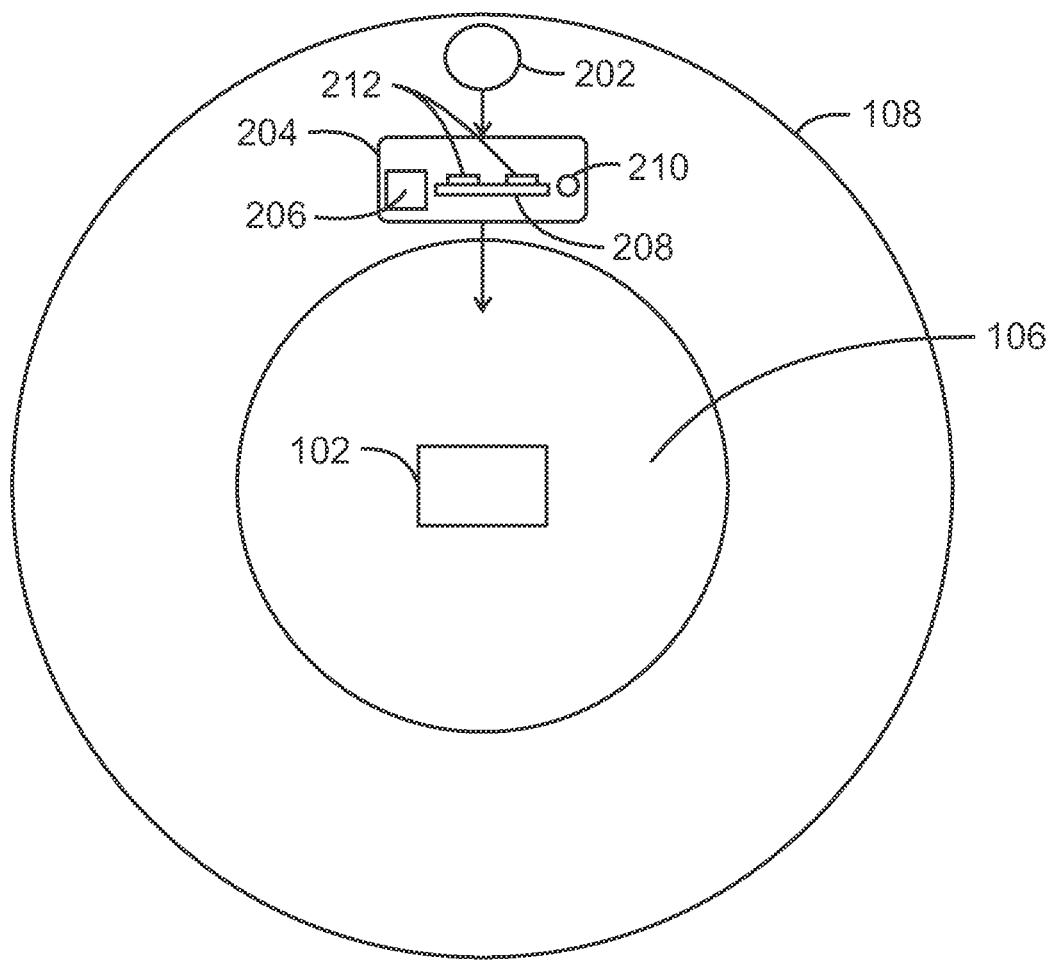
FIG. 2 illustrates a front view of a gantry having a radiation emitter and a collimator.

FIG. 2 illustrates a front view of a gantry having a radiation emitter and a collimator. The subject 102 may be placed in, or travel through, the bore 106 of the gantry 108. A radiation emitter 202 may emit radiation towards the subject 102, as indicated in FIG. 2. The radiation emitted passes through a collimator 204. The collimator 204 may be configured to narrow a beam of particles or waves. The collimator 204 narrows radiation emitted from the radiation emitter 202 towards the subject, based on various image capture protocols associated for a desired imaging result.

Although only one of each is shown in the view of FIG. 2, the collimator 204 includes two motors, such as the motor indicated at 206, two actuators, such as the actuator indicated at 208, and two position detection modules, such as the position detection module indicated at 210. In embodiments, a position detection module 210 may be referred to herein as an "encoder." Both motors, including the motor 206, are located on the same side of the actuators, including the actuator 208. Likewise, both encoders, including the encoder 210, are located on the same side of the actuators, including the actuator 208.

The disposition of the motors, including the motor 206, on the same side provides a lower spatial footprint of the collimator 204. As discussed in more detail below, the collimator 206 may enable independent motion of plates 212 attached to the actuators, while still preserving a lower spatial footprint of the collimator 204 than if motors, including one of the motors 206, were disposed on opposite sides of the actuators, including the actuator 208. The plates 212 may be composed of a radiation absorbing material. An example of a radiation absorbing material may include lead. Another example of a radiation absorbing material may include tungsten. In any case, the plates 212 may move in order to widen or narrow the radiation emitted through the collimator 206.

Figure 3:
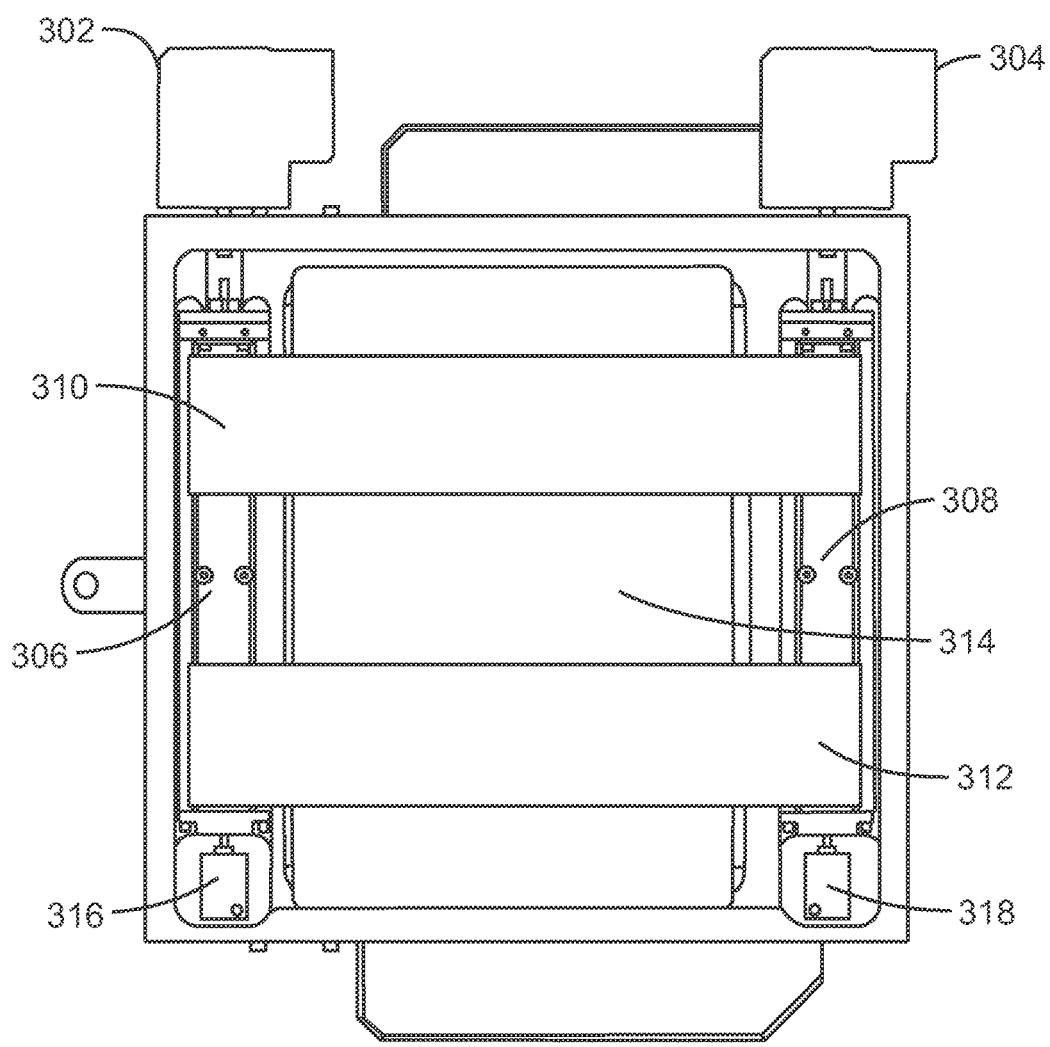
FIG. 3 illustrates a diagram of an actuator system for adjusting an aperture of a collimator.

FIG. 3 illustrates a diagram of an actuator system for adjusting an aperture of a collimator. The actuator system 300 includes motors 302 and 304. Each of the motors 302 and 304 are coupled to actuator assemblies 306 and 308, respectively. The actuator assemblies 306 and 308 are substantially parallel to each other. Moving plates, 310 and 312, are substantially perpendicular to the parallel actuator assemblies 306 and 308. The moving plates 310 and 312 are used to adjust a size of an opening defined by the moving plates, indicated by the arrow 314. The plates 310, 312, are coupled to the actuator assemblies 306, 308, in a manner to allow independent motion of each plate, as discussed in more detail below in regard to FIG. 4.

The actuator system 300 also includes encoders 316 and 318. The encoders 316 and 318 may provide position information of each of the moving plates 310 and 312 to a controller, or processing unit, of the collimator 204 of FIG. 2, or other computer-implemented processing device of the imaging system 100 of FIG. 1. In some embodiments, the encoders 316 and 318 may be linear scales substantially parallel to the actuator assemblies 306 and 308, respectively.

As illustrated in FIG. 3, the motors 302 and 304 are disposed on a same side with respect to the actuator assemblies 306 and 308. Similarly, the encoders 316 and 318 are disposed on a same side of the actuator assemblies 306 and 308. In embodiments, the encoders 316 and 318 are disposed on a side that is opposite to the side at which the motors 302 and 304 are disposed. However, the encoders 316 and 318 may, in some scenarios, be disposed on the same side as the motors 302 and 304, as may be understood by one having skill in the art. As discussed above, the moving plates 310 and 312 may be independently controlled by a respective motor, either 302 or 304, depending on a given configuration. As discussed in more detail below, the moving plates 310 and 312 may be configured to each have one carriage engaged with one actuator, and another carriage free-floating, or otherwise disengaged from the other actuator.

Figure 4:
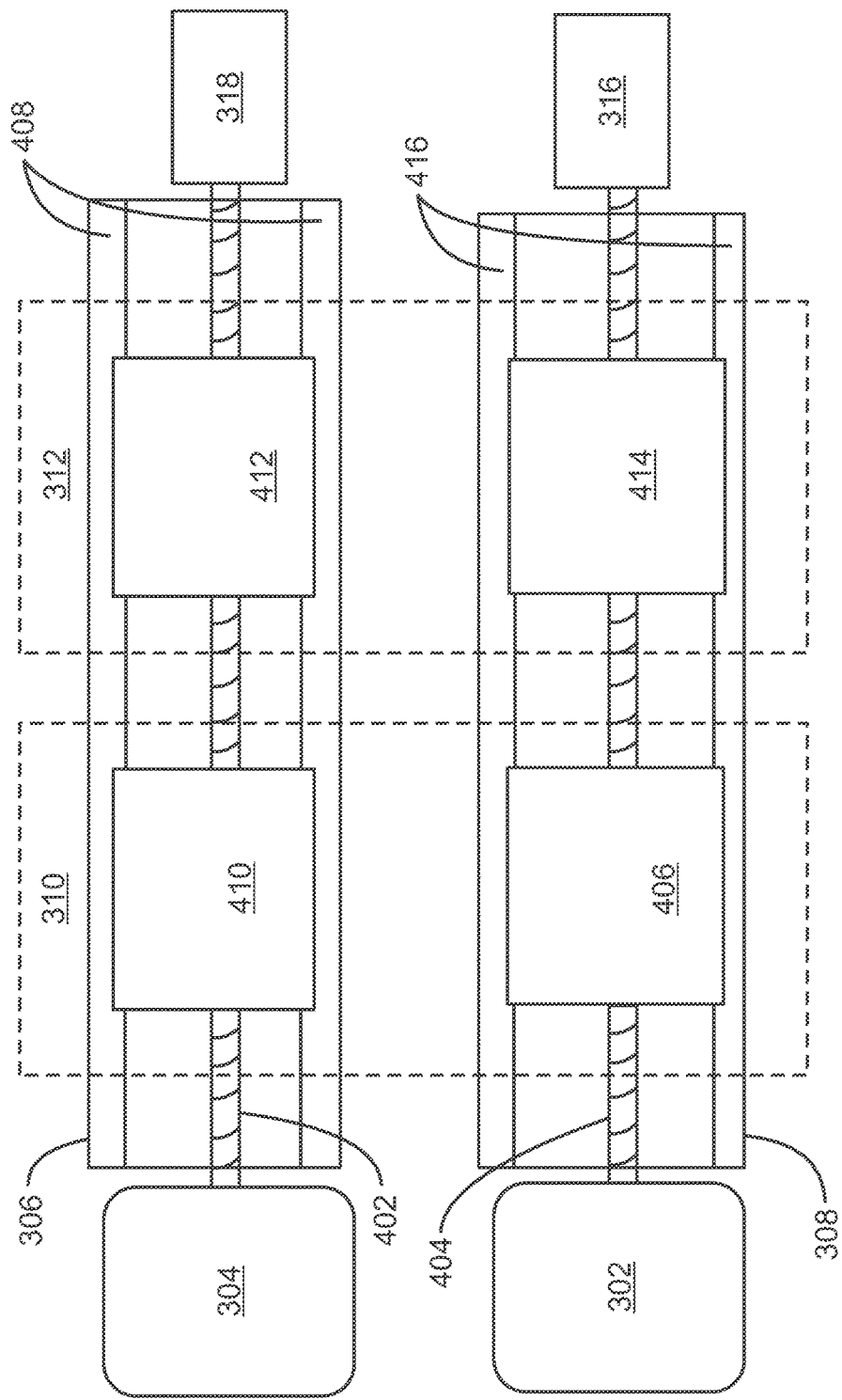
FIG. 4 illustrates a top view of a diagram of an actuator system having independent movement of moving plates.

FIG. 4 illustrates a top view of a diagram of an actuator system having independent movement of moving plates. The actuator system 400 illustrated in FIG. 4 is similar to the actuator system 300 illustrated in FIG. 3. Therefore, similar elements may retain similar reference numerals. The actuator system includes the motors 302 and 304, the actuator assemblies 306 and 308, the moving plates 310 and 312, and the encoders 316 and 318.

As illustrated in FIG. 4, the moving plates 310 and 312 are illustrated as dashed boxes representing a transparent view of the moving plates 310, 312. Each of the moving plates 310 and 312 may be attached to a linear actuator 402 and 404, respectively, by a driving carriage. The motor 304 may engage the linear actuator 402 at an axis of the first linear actuator 402. The motor 302 may engage the second linear actuator 404 at an axis of the second linear actuator 404.

The moving plates 310 and 312 may be moved independently by engagement of the motors 302, 304, and in cooperation of a respective driven carriage, such as driven carriage 406 and/or driven carriage 412. Specifically, the moving plate 310 may be attached to linear actuator 404 by the driven carriage 406. In contrast, the moving plate 310 may be unengaged with the linear actuator 402, but may be travel along guiderails 408 of the actuator assembly 306 as a result of a free carriage 410 attached to the moving plate 310. In embodiments, the free carriage 408 may include bearings enabling motion of the free carriage 410 may along the guiderails 408. Similarly, the moving plate 312 may be driven by the linear actuator 402 by way of the driven carriage 412 engaged with the linear actuator 402. A free carriage 414 may enable the moving plate 312 to be free from motion caused by the linear actuator 404, but may include bearings for free motion of the moving plate 312 along guiderails 416 of the actuator assembly 308.

The arrangement illustrated in FIG. 4 enables independent motion of one of the moving plates 310 and 312, without engaging or causing motion of the other plate. For example, the motor 302 may turn, causing the linear actuator 404 to rotate. In embodiments, the linear actuator 404 is a ball screw, and the drive carriage 406 includes a drive nut (not shown) configured to engage with the ball screw. The rotation of the motor 302 therefore causes motion of the moving plate 310. During motion, the free carriage 410 may move without engaging, or impinging upon the linear actuator 402, but instead moving freely along the guiderails 408, and, therefore, independent motion of the moving plate 310 may be accomplished. As another example, the moving plate 312 may be moved by the motor 304 engaging the linear actuator 402. The linear actuator 402 may be a ball screw, and the drive carriage 412 may include a drive nut configured to engage with the ball screw, similar to the drive carriage 406. Likewise, the free carriage 414 may be similar to the free carriage 410 as the free carriage 412 is disengaged with the linear actuator 404, but floats freely along the guiderails 416.

Further, as discussed above, and as illustrated in FIG. 4, the motor 304 and the motor 302 are disposed on the same side in relation to the actuator assemblies 306 and 308, as opposed to being disposed on opposite sides. The arrangement illustrated in FIG. 4 enables a smaller over all spatial foot print than if the motors 302, 304 were to be disposed on opposite sides. For example, placing motors 302 and 304 on opposite sides of the actuator assemblies 306 and 308 may create additional width of a collimator 204 of FIG. 2. Instead, the techniques described herein allow for both the motors 302 and 304 to be disposed on the same side with respect to the actuator assemblies 306 and 308, thereby reducing the width of a collimator, such as the collimator 204 of FIG. 2. The disposition of the motors 302, 304 on the same side in relation to the actuators 306, 308 is, in embodiments, enabled by the arrangement of the carriages 406, 408, 410, and 412 of the moving plates 310 and 312.

Figure 5:
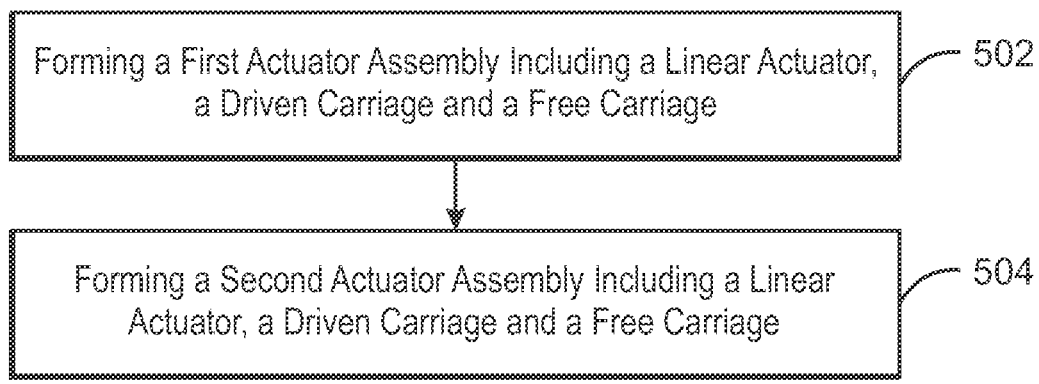
FIG. 5 is a block diagram a method of manufacturing an independent actuator motion apparatus.

FIG. 5 is a block diagram a method of manufacturing an independent actuator motion apparatus. The method 500 includes forming a first actuator assembly including a linear actuator, a driven carriage, and a free carriage. The linear actuator may be a first linear actuator, the driven carriage a first driven carriage, and the free carriage a first free carriage. The first free carriage may be disengaged from motion associated with the first linear actuator, while the first driven carriage may be configured to be driven by the first linear actuator.

The method 500 may continue at 504 where a second actuator assembly is formed. The second actuator assembly may include a linear actuator, a driven carriage, and a free carriage. For clarity, the linear actuator of the second actuator assembly may be a second linear actuator, the driven carriage a second drive carriage, and the free carriage a second free carriage.

Although not illustrated in FIG. 5, the method 500 may include coupling a first motor to drive the first linear actuator, and a second motor to drive the second linear actuator. The linear actuators are disposed substantially parallel to one another, and the motors may be disposed on the same side of the parallel linear actuators. As discussed above, the disposition of the motors on the same side of the parallel linear actuators may reduce the overall physical footprint of the actuator assembly, and/or the collimator in which the actuator assembly may be placed.

The method 500 may also include coupling a first encoder to the first actuator assembly, and a second encoder to the second actuator assembly. The encoders may be position detection modules configured to provide plate position information to a controller of an imaging system. For example, the encoders may be communicatively coupled to hardware and/or software configured to determine the position of each moving plate based on signals and/or other indicators provided by the encoders.

While examples and descriptions of the techniques described herein are in reference to an imaging system, such as the imaging system 100 discussed above in regard to FIG. 1, the techniques may be implemented in various other systems wherein parallel linear actuators are used. Further, when parallel linear actuators are used in combination with perpendicular attaching components, such as the moving plates discussed above, the techniques described herein may provide independent motion of the moving plates without increasing an overall physical footprint.

While the detailed drawings and specific examples given describe particular embodiments, they serve the purpose of illustration only. The systems and methods shown and described are not limited to the precise details and conditions provided herein. Rather, any number of substitutions, modifications, changes, and/or omissions may be made in the design, operating conditions, and arrangements of the embodiments described herein without departing from the spirit of the present techniques as expressed in the appended claims.

This written description uses examples to disclose the techniques described herein, including the best mode, and also to enable any person skilled in the art to practice the techniques described herein, including making and using any devices or systems and performing any incorporated methods. The patentable scope of the techniques described herein is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. An apparatus for independent actuator motion, comprising:
    a first linear actuator;
    a first driven carriage to be driven by movement of the first linear actuator; and
    a first free carriage in line with the first linear actuator but being disengaged from the first linear actuator motion;
    a first pair of guide rails flanking the first linear actuator, wherein each guide rail of the first pair of guide rails directly engages both the first driven carriage and the first free carriage;
    a second linear actuator substantially parallel to the first linear actuator;
    a second driven carriage to be driven by movement of the second linear actuator; and
    a second free carriage in line with the second linear actuator but being disengaged from the second linear actuator motion and to be coupled to the first driven carriage; and
    a second pair of guide rails flanking the second linear actuator, wherein each guide rail of the second pair of guide rails directly engages both the second driven carriage and the second free carriage.

2. The apparatus for independent actuator motion of claim 1, wherein the plates are components of a collimator aperture.

3. The apparatus for independent actuator motion of claim 1, wherein the second free carriage is to be driven by movement of the first driven carriage.

4. The apparatus for independent actuator motion of claim 1, wherein the first free carriage is coupled to the second driven carriage, and wherein the first free carriage is to be driven by movement of the second driven carriage.

5. The apparatus for independent actuator motion of claim 1, further comprising:
    a first motor to engage a first actuator assembly at an axis of the first linear actuator; and
    a second motor to engage a second actuator assembly at an axis of the second linear actuator.

6. The apparatus for independent actuator motion of claim 5, wherein the first motor and second motor are disposed on a same side relative to the actuator assemblies.

7. The apparatus for independent actuator motion of claim 6, wherein the first and second actuator assemblies are to couple to position detection modules in line with the axis of the linear actuators of each assembly respectively, and on a side opposite to the motors.

8. The apparatus for independent actuator motion of claim 1, wherein the linear actuator comprises a ball screw.

9. The apparatus for independent actuator motion of claim 1, wherein the first driven carriage and the first free carriage are directly coupled to the first linear actuator.

10. The system for independent actuator motion of claim 1, wherein the first free carriage does not contact the first linear actuator.

11. A system for independent actuator motion, comprising:
- a first actuator assembly comprising:
  - a first linear actuator;
  - a first driven carriage to be driven by the first linear actuator; and
  - a first free carriage disengaged from motion associated with the first linear actuator;
  - a first pair of guide rails flanking the first linear actuator, wherein each guide rail of the first pair of guide rails directly engages both the first driven carriage and the first free carriage; and
- a second actuator assembly substantially parallel to the first actuator assembly, the second actuator assembly comprising:
  - a second linear actuator;
  - a second driven carriage to be driven by the second linear actuator; and
  - a second free carriage disengaged from motion associated with the second linear actuator and to be coupled to the first driven carriage of the first actuator assembly; and
  - a second pair of guide rails flanking the second linear actuator, wherein each guide rail of the second pair of guide rails directly engages both the second driven carriage and the second free carriage.

12. The system for independent actuator motion of claim 11, further comprising:
- a first motor to engage the first actuator assembly at an axis of the first linear actuator; and
- a second motor to engage the second actuator assembly at an axis of the second linear actuator.

13. The system for independent actuator motion of claim 12, wherein the first motor and second motor are disposed on a same side relative to the actuator assemblies.

14. The system for independent actuator motion of claim 13, wherein the first and second actuator assemblies are to couple to position detection modules in line with the axis of the linear actuators of each assembly respectively, and on a side opposite to the motors.

15. The system for independent actuator motion of claim 11, wherein the linear actuator comprises a ball screw.

16. A method of manufacturing an independent actuator motion apparatus, comprising:
- forming a first actuator assembly comprising:
  - a first linear actuator;
  - a first carriage to be driven by the first linear actuator; and
  - a second carriage disengaged from motion associated with the first linear actuator;
  - a first pair of guide rails flanking the first linear actuator, wherein each guide rail of the first pair of guide rails directly engages both the first carriage and the second carriage; and
- forming a second actuator assembly substantially parallel to the first actuator assembly, the second actuator assembly comprising:
  - a second linear actuator;
  - a third carriage to be driven by the second linear actuator;
  - a fourth carriage disengaged from motion associated with the second linear actuator and to be coupled to the first carriage of the first actuator assembly; and
  - a second pair of guide rails flanking the second linear actuator, wherein each guide rail directly engages both the third carriage and the fourth carriage.

17. The method of manufacturing independent actuator motion of claim 16, further comprising:
- coupling a first motor to the first actuator assembly at an axis of the first linear actuator; and
- coupling a second motor to the second actuator assembly at an axis of the second linear actuator, wherein the first motor and second motor are disposed on a same side relative to the actuator assemblies.

18. The method of manufacturing independent actuator motion of claim 16, further comprising:
- coupling a first encoder to the first actuator assembly to determine a position of a plate disposed upon the apparatus; and
- coupling a second encoder to the second actuator assembly to determine a position of another plate disposed upon the apparatus.

* * * * *